United States Patent [19]

Sibalis

[11] Patent Number: 5,032,109
[45] Date of Patent: * Jul. 16, 1991

[54] ELECTROLYTIC TRANSDERMAL DELIVERY OF POLYPEPTIDES

[75] Inventor: Dan Sibalis, Stony Brook, N.Y.

[73] Assignee: Drug Delivery Systems Inc., New York, N.Y.

[*] Notice: The portion of the term of this patent subsequent to Nov. 7, 2006 has been disclaimed.

[21] Appl. No.: 430,067

[22] Filed: Nov. 1, 1989

Related U.S. Application Data

[63] Continuation of Ser. No. 360,277, Jun. 1, 1989, abandoned, which is a continuation of Ser. No. 12,889, Feb. 10, 1987, Pat. No. 4,878,892.

[51] Int. Cl.$^5$ .............................................. A61M 37/00
[52] U.S. Cl. ...................................... 604/20; 128/798; 424/449
[58] Field of Search ................... 604/20; 128/798, 799; 424/447–449

[56] References Cited

U.S. PATENT DOCUMENTS

| | | | |
|---|---|---|---|
| 4,416,274 | 11/1983 | Jacobsen et al. | 604/20 |
| 4,459,226 | 7/1984 | Grimes et al. | 260/112.7 |
| 4,624,665 | 11/1986 | Nuwayser | 604/307 |
| 4,702,732 | 10/1987 | Powers et al. | 604/20 |
| 4,704,282 | 11/1987 | Campbell et al. | 424/449 |
| 4,710,497 | 12/1987 | Heller et al. | 514/947 |
| 4,713,244 | 12/1987 | Bawa et al. | 424/429 |
| 4,725,439 | 2/1988 | Campbell et al. | 424/449 |
| 4,731,049 | 3/1988 | Parsi | 604/20 |
| 4,752,285 | 6/1988 | Petelenz | 604/20 |
| 4,767,401 | 8/1988 | Seiderman | 604/20 |
| 4,786,278 | 11/1988 | Masaki | 604/20 |
| 4,878,892 | 11/1989 | Sibalis et al. | 604/20 |
| 4,940,456 | 7/1990 | Sibalis et al. | 604/20 |

FOREIGN PATENT DOCUMENTS

| | | | |
|---|---|---|---|
| 0252732 | 1/1988 | European Pat. Off. | 128/1 R |
| 591194 | 2/1978 | U.S.S.R. | 604/20 |
| 620265 | 8/1978 | U.S.S.R. | 604/20 |
| 978835 | 12/1982 | U.S.S.R. | 604/20 |
| 1017348 | 5/1983 | U.S.S.R. | 604/20 |
| 1076124 | 2/1984 | U.S.S.R. | 604/20 |

OTHER PUBLICATIONS

Shaya et al., "Percutaneous electrophoresis of amino acids and urea", Med. & Biol. Eng. & Comput., Mar. 1978, 16, 126–134.
The Merck Index, 1976.

*Primary Examiner*—C. Fred Rosenbaum
*Assistant Examiner*—Mark O. Polutta
*Attorney, Agent, or Firm*—Lackenbach Siegel Marzullo & Aronson

[57] ABSTRACT

The invention comprises in combination:
(a) a polypeptide having from about three to about 20 peptide units in aqueous solution or suspension, and
(b) an electrolytic device for transdermal transport of the polypeptide to the bloodstream of the patient.

It may be useful to enhance the transdermal delivery of the polypeptide by adding an aqueous cosolute/cosolvent with negative Setschenow constants.

The electrolytic device preferably comprises a hydrophilic reservoir containing a supply of the aqueous polypeptide solution or suspension, an electric battery, two extended contacts, and optionally a semipermeable membrane between the reservoir and the patient's skin.

Representative polypeptides include oxytocin, angiotensin I, II, and III, substance P, vasopressin, lypressin, desmopressin, leuprolide acetate, antripeptin, and the like.

26 Claims, 1 Drawing Sheet

ELECTROLYTIC TRANSDERMAL DELIVERY OF POLYPEPTIDES

RELATED U.S. PATENTS AND APPLICATIONS

This application is a continuation of application Ser. No. 360,277, filed June 1, 1989, abandoned, which is a continuation of Ser. No. 012,889, filed Feb. 10, 1987, now U.S. Pat. No. 4,878,892.

This application is related to U.S. Pat. Nos. 4,557,723, 4,622,031 and 4,640,689 and to copending applications Ser. No. PCT/US85/00080 filed Jan. 17, 1985; PCT/US85/01074 and PCT/US85/01075 both filed June 10, 1985; Ser. No. 778,183 filed Sept. 16, 1985 now U.S. Pat. No. 4,708,766; Ser. No. 807,234 filed Dec. 10, 1985 now U.S. Pat. No. 4,731,926; Ser. No. 839,523 filed Mar. 14, 1986 abandoned; Ser. No. 888,151 filed July 18, 1986 abandoned; Ser. No. 922,296 filed Oct. 23, 1986 abandoned; and Ser. No. 07/000,554 and 07/000,555 filed Jan. 5, 1987, now U.S. Pat. No. 4,808,152 and abandoned, respectively.

FIELD OF THE INVENTION

This invention relates to electrolytic transdermal delivery of polypeptides and more specifically to delivery to the blood stream of the patient of aqueous solutions of suspensions containing polypeptides with from about three to about 20 alphaamino acid units.

BACKGROUND OF THE INVENTION

Patents and patent applications cited above disclose basic aspects of transdermal delivery of drugs by electrical power patches on the patient's skin. Other U.S. and foreign patents also disclose transdermal electrical, and medical effects, as follows:

| U.S. Pat. Nos. | | |
|---|---|---|
| 385,556 | 2,267,162 | 3,163,166 |
| 486,902 | 2,493,155 | 3,289,671 |
| 588,479 | 2,784,715 | 3,547,107 |
| 3,677,268 | 4,239,052 | 4,367,745 |
| 4,008,721 | 4,243,052 | 4,367,745 |
| 4,141,358 | 4,273,135 | 4,406,658 |
| 4,164,226 | 4,290,878 | 4,419,019 |
| 4,166,457 | 4,325,367 | 4,474,570 |
| 4,239,046 | 4,362,645 | |
| Foreign Patents | | |
| EPA 58,920 | DE 2,902,021.83 | UK 2,104,388 |
| EPA 60,452 | DE 3,225,748 | |

None of these references, however, show the effective administration of polypeptide drugs such as desmopressin, vasopressin, substance P, angiotensin, lypressin and the like.

OBJECTS OF THE INVENTION

It is an object of the present invention to administer polypeptide drugs with a range of molecular weights from about three peptide units to about 20 peptide units transdermally to humans, adult or child, and other animal patients by means of a locally applied electric field.

It is a further object of the invention to administer polypeptide drugs transdermally in an electric field regardless of the degree of ionization or the amount of ionic charge on the polypeptide.

It is yet another object to maximize the transdermal administration of polypeptide drugs by eliminating or minimizing the association of polypeptide drugs in aqueous media.

It is still another object to administer polypeptide drugs transdermally by an electric applicator which occupies minimal area, gives the patient minimal discomfort, generates sufficient current density with minimal size and weight, and operates effectively under a wide variety of skin conditions.

It is yet a further object to administer polypeptide drugs transdermally by electrolytic devices without irritation or reddening of the skin, and without tingling or other sensations.

Other objects of the present invention will be apparent to those skilled in the art.

SUMMARY OF THE INVENTION

The present invention comprises in combination:
(a) a polypeptide having from about three to about 20 peptide units in aqueous solution or suspension, and
(b) an electrolytic device for transdermal transport of the polypeptide to the bloodstream of the patient.

The invention further comprises a method for delivering the polypeptide to the bloodstream of the patient by means of the electrolytic device.

The polypeptide may be of homopolymeric, heteropolymeric, cyclical, or other structural type.

It may be useful to enhance the transdermal delivery of the polypeptide by adding an aqueous cosolute/cosolvent with negative Setschenow constants.

The electrolytic device preferably comprises a hydrophilic reservoir containing a supply of the aqueous polypeptide solution or suspension, an electric battery, two extended contacts, and optionally a semipermeable membrane between the reservoir and the patient's skin.

Representative polypeptides include oxytocin, angiotensin I, II, and III, substance P, vasopressin, lypressin, desmopressin, leuprolide acetate, and the like. Within the scope of this invention is the transdermal delivery of polypeptides with other classes of drugs, such as steroids.

DESCRIPTION OF THE PREFERRED EMBODIMENTS OF THE INVENTION

Figure 1:
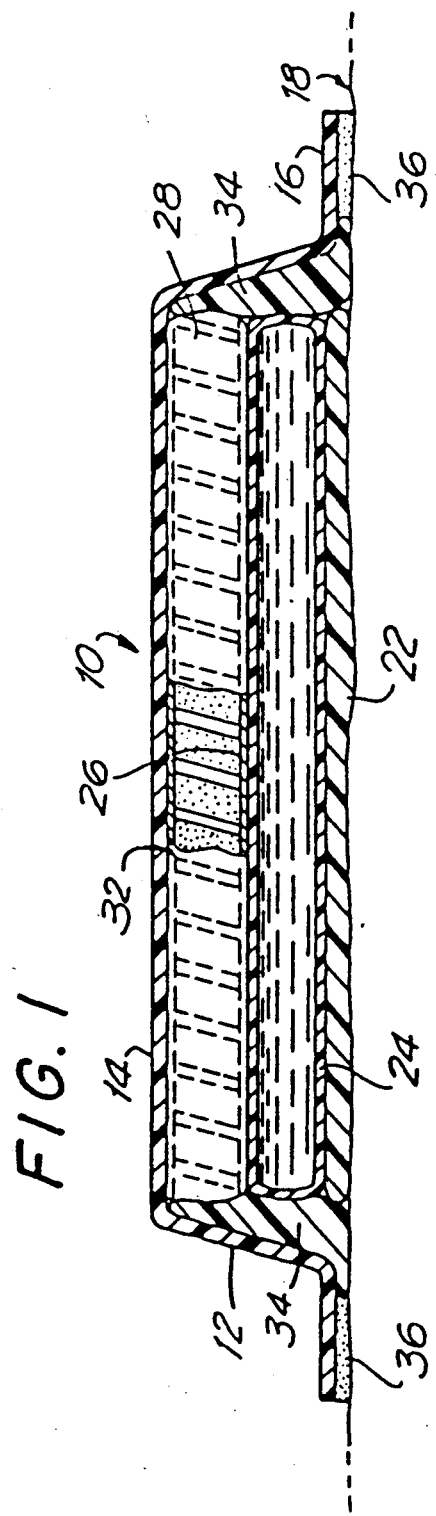
FIG. 1 is a cross-sectional view of one type of electronic/electrolytic device to administer polypeptides to a patient transdermally.

Polypeptides are condensation polymers of aminoacids which are linked by formation of amide bonds from the amino group of one aminoacid and the carboxylic acid group of another. Polypeptides are homopolymers or heteropolymers of the 20 aminoacids necessary to build mammalian body tissue. In nature, they have a laevo configuration. In this disclosure "polypeptide" means molecules with from about three to about 20 peptide units or amino acids.

In copending application Ser. No. 07/012,898, filed concurrently on Feb. 10, 1987 abandoned. I disclose an invention for administering "proteins" transdermally by electrolytic means and define "protein" as a polypeptide with more than about 20 peptide units, e.g. insulin whose single-strand has 51 units.

Numerous polypeptides are useful drugs in the treatment of human diseases or their diagnosis. Table I shows examples of the names of drugs, their trade names, and their application.

TABLE I

Some Polypeptide Drugs

| Name | Trade-name(s) | No. of Peptide Units | Application |
|---|---|---|---|
| vasopressin | Pitressin | 9 | diabetes insipidus GI hemmorhage |
| desmopressin | DDAVP | 9 | diabetes insipidus |
| oxytocin | Pitocin | 9 | induction of labor |
| lypressin | Diapid | 9 | antidiuretic |
| leuprolide acetate | Lupron | 9 | prostate cancer LH-RH FSH inhibitor |
| dynorphin A | (1-17) | 17 | peptide opioides are analgesics |
| dynorphin A | (1-8) | 8 | |
| dynorphin B | | 13 | |
| met-enkephalin | | 5 | |
| leu-enkephalin | | 5 | |
| thyrotropin releasing hormone | TRH | 3 | clinical diagnostic |
| | MIF | 3 | |
| α-melanocyte stim. hormone | α-MSH | 13 | hormonal regulator |
| β-melanocyte stim. hormone | β-MSH | 18 | hormonal regulator |
| neurotensin | | 13 | insulin regulator |
| substance P | | 11 | analgesic |
| somatostatin | | 14 | growth hormone inhib |
| angiotensin I | | 10 | modulate blood pressure |
| II | | 8 | |
| III | | 7 | |
| atriopeptin | | 21 | fluid regulation |

It should be emphasized that polypeptides can vary widely in the number of peptide units they contain from a few, as in thyrotropin releasing hormone to six times 51 units as in hexameric insulin. In order for large polypeptides to be transported through the skin, it is preferable that the polypeptide be unassociated. If the polypeptide is single-stranded, the cross-section of the linear macromolecular would be only a few square Angstoms even if the entire folded, convoluted, or random polymer is large in radius of gyration. It is sometimes preferable to add a dissociating agent to a solution of the smaller polypeptides of the present invention, also.

There have been many proposed descriptive models for the structure of liquid water, such as:
(a) in interstitial model of ice whose cavities are filled with water,
(b) quartz-like aggregates,
(c) water as a hydrate of itself,
(d) flickering clusters of cooperative H-bonds;
(e) a two-structure, mixture model.

Chemists have known for decades that water forms clathrates with xenon, chlorine, methane and other molecules and therefore must have cavities. The structure of liquid water depends on the distance and angles of H-bonds. In a two-dimensional sense, water is a hexagonal array of "aromatic" structures.

The solubility of argon in "structured" water is about one-tenth that of argon in alcohols. As temperature increases from 0° to 30° C. the solubility of argon in water decreases while that in alcohols increases. The charge in entropy of methane in water is about −15 to −20 e.u. but in alcohols, dioxane, and cyclohexane is about −1 e.u. The change in enthalpy of methane in water is about −3000 cal/mole, but in the same organics is 200–500 cal/mole. The process of solution may be modeled as "forming a cavity" then introducing the solute into that cavity. In a normal fluid the energy to form the cavity is positive, then filling the cavity is minus (attractive). Since water already has cavities present, there is about zero energy to form such and negative energy to dissolve the solute (fill) the cavity.

Adding some nonpolar nonelectrolytes such as ether, methyl acetate, dimethylsulfoxide structure water i.e. reinforce water structure and decrease its compressibility. Some small ions e.g. lithium and fluoride also reinforce the structure of water.

Conversely, most ions, iodine, methyl halides, small aminoacids, urea, and other polar nonelectrolytes are "structure breakers" of water.

Precise analysis of the structure of water may be a complex matter, yet it is a description of only one substance. Precise description of polypeptides dissolving in water, or dissociating if already dissolved, covers much broader phenomena, since there are myriad polypeptides and myriad cosolvents or dissociation agents to coact with water.

The conformation of polypeptides in solution is dependent at a minimum on the concentration of polypeptide, pH, solvent composition, ionic strength, ionic charge on the polypeptide, solvent dielectric properties, presence of cosolutes, shear stresses, and the presence of heterogeneous third bodies such as surfaces of the container, granules, and the like.

It is generally accepted that the configuration of polypeptides in aqueous media comprises folded macromolecules with hydrophopic domains forming a central core and hydrophilic domains oriented toward the aqueous perimeter. The process of dissolution is difficult to describe in detail, but the energetics of the solution process can be determined in a straightforward manner. Much information about solution, disassociation, denaturation, coiling, gelation, unfolding, and other changes in so-called tertiary and quaternary structures may be gained from a detailed study of solution and/or gelation of polypeptides in water and water containing other cosolvents or "agents".

The primary structure of a polypeptide is the term used for the sequence of aminoacids as they appear along the chain of the macromolecule. The local organization of the chain e.g. helix formation, random coil, folding is termed secondary structure. The overall spatial arrangement of the polypeptide on the atomic level, what X-ray crystallography shows, is the tertiary level of structure. The quaternary structure is that of several chains which may form different regions with different properties e.g. a dumbbell-like structure with a flexible middle rod and two hard ends. The function of the regions may vary. In hemoglobin, 4 myoglobins group to form a dumbbell shape with a molecular weight of about 17,000 daltons with the oxygen-bearing function associated with the two harder spheres on the ends rather than the flexible part in the middle.

Dissociation agents greatly affect quaternary structure, are irrelevant to tertiary structure, may affect secondary structure, and have no effect on primary structure of polypeptides.

The effect of a solvent such as water on a polypeptide can be described in terms of an equilibrium constant $K_D$ and the standard free energy of dissociation $\Delta F°$, when a polypeptide dissociates from e.g. hexamers to dimers or single-stranded subunits e.g. insulin in water. Often these different fragments can coexist in a series of equilibria e.g. earthworm hemoglobin duodecamers, hexamers, tetramers, dimers, and single fragments, at intermediate concentrations of a pure solvent or one with a dissociation agent such as propylurea or sodium perchlorate present. When such an added dissociation cosolvent is present there are two dissociation constants $K_{DW}$ and $K_{DAW}$, where DW designates pure water and DAW designates added agent and water. The interaction of the added agent and the polypeptide involves the binding constant $K_B$.

For polypeptides binding constant $K_B$ is the summation of two terms: a polar component $K_P$ related to the peptide bond —NHCOO— and a hydrophobic component $K_H$ related to the average hydrophobic moiety —CHR— different for each aminoacid but averagable. The constant is related to energetics by the Nernst equation. So $$F^{\circ}{}_{DW} = F^{\circ}{}_{DAW} - mNRT(K_p + K_H)[da],$$

when m is the number of fragments and N is the number of binding sites and [da] is the concentration of the dissociation cosolvent.

When a solid polypeptide is in contact with a well-stirred solvent such as water for a long time (e.g. a week) an equilibrium saturated solution is established:

$$K_{eq} = -RT\ln C_{sat}$$

When another compound is added to the water, such as an electrolyte or a nonelectyrolyte, a different $C_{sat}$ is established at equilibrium. This other value will normally be different from $C_{sat}$ for pure water. The higher the concentration of the added agent, the higher (or lower) the saturated concentration of the polypeptide. When one graphs the log $C_{sat}$ against the molarity of the added agent, a straight line is formed. The slope of this straight line is known as the Setschenow constant for the agent. Since the equation above has a minus sign in it, those agents which aid solubility and dissociation, e.g. urea, have a negative Setschenow constant, and those agents which decrease solubility and dissociation, e.g. sodium or ammonium sulfate have positive Setschenow constants.

$$K_s \approx -K_B/2.303$$

The Setschenow constant $K_s$ has peptide and hydrophobic components. The Setschenow constant can be approximated by negative $K_B$ divided by log transform constant 2.303. Since negative standard free energies of transfer indicate spontaneous reactions, negative F° values for transfer from water to a mixture of water and the cosolvent indicate dissociation. The more negative, the more dissociated. Table II gives Setschenow constants for average peptide and hydrophobic groups as well as free energy of transfer values for a variety of cosolvents, as taken from a paper by Herkovits et al., Journal of Colloid and Interface Science, vol. 63, No. 2, p. 232 of February 1978. The lower the position in Table II, the better the dissociation agent.

Since thermodynamics is a description of the ultimate reality, the last column listing free energies of transfer shows those agents which are preferred in practicing the present invention, those agents with negative standard free energies. The Setschenow constants are helpful, however, in appreciating how the agent is useful. The "sum" column of interaction with peptide linkages in the polypeptide plus the interaction with the hydrophobic moieties is directly linked to the free energy column by the Nernst equation. It is the peptide interaction number and the hydrophobic or "methylene" number, which show how a dissociation agent works.

TABLE II

| Agent | Setschenow Constants | | | -F.° cal/mo |
|---|---|---|---|---|
| | For peptide | For —CH2— | Sum | |
| Sodium sulfate | -0.013 | 0.085 | 0.072 | 98 |
| Potassium fluoride | -0.027 | 0.05 | 0.023 | 31 |
| Ethanol | +0.037 | -0.014 | 0.023 | 31 |
| Dioxane | +0.029 | -0.013 | 0.016 | 22 |
| Sodium chloride | -0.037 | 0.033 | -0.004 | -5 |
| Sodium acetate | — | — | -0.009 | -12 |
| Sodium bromide | -0.037 | 0.025 | -0.012 | -16 |
| Calcium chloride | -0.077 | 0.063 | -0.014 | -19 |
| Sodium proprionate | — | — | -0.017 | -23 |
| Urea | -0.018 | -0.01 | -0.028 | -38 |
| Sodium butyrate | — | — | -0.038 | -51 |
| Propylurea | — | — | -0.047 | -64 |
| Sodium thiocyanate | -0.077 | 0.007 | -0.07 | -96 |
| Potassium iodide | -0.083 | 0.01 | -0.073 | -100 |
| Sodium perchlorate | -0.097 | 0.021 | -0.076 | -104 |
| Sodium iodide | -0.087 | 0.01 | -0.077 | -105 |
| Guanidine hydrochloride | -0.061 | -0.027 | -0.088 | -120 |

Urea, guanidine hydrochloride, or any other compound which has two negative parameters interact with the entire polypeptide to disaggregate any quaternary structure and perhaps unfold the secondary structure. This type of dissociating agent may be helpful in practicing the present invention of delivering polypeptides with from abaout three to about 20 peptide units to the bloodstream of the patient. Sodium perchlorate, potassium iodide, and the like interact so strongly with peptide bonds that their lack of interaction with hydrophobic linkages of the polypeptide does not appreciably inhibit dissociation of the polypeptide. These agents may be useful in practicing the present invention. Ethanol, dioxane and other organics strongly react with the hydrophobic moieties, but not enough to overcome the nonpolar nature of organic solvents. Data on ethanol diverges, however. Such agents have limited utility in practicing this invention. Agents which have two positive components for their Setschenow constant and hence a positive standard free energy of transfer do not appear on Table II.

Electrophoresis is the transport of both solute and solvent in an electric field. Ionophoresis is the transport of charged ions by coulombic attraction/repulsion in an electric field. Electroosmosis is the transport of solvent in an electric field.

Many workers in the prior art overemphasized ionophoresis and underestimated electroosmosis in their analysis of both the best modes for and problems associated with transdermal delivery of drugs by electrolytic means. In fact, the essence of transdermal, electric-powered delivery of drugs is that control and maximization is central regardless of whether the drug is transported by coulombic attraction/repulsion or electroosmotic solvent streaming. In the present invention, unlike the prior art, Faraday's law is irrelevant. In many situations, more drug is carried by electroosmosis than ionophoresis, so that the amount of charge or degree of ionization of the polypeptide is not important. Before the present invention this fact was not appreciated. Prior workers attempted to improve ionophoresis by increasing charge density on the polypeptide by oxidation or hydrolysis. For this invention the value of charge density on the drug does not control the dosage.

Electronic conduction is the movement of electrons in an electric field. Electrolytic conduction is the movement of ions in an electric field. Prior to the present invention, many workers failed to communicate their results well or to explain their ideas well because of confusion regarding the flow of electrons and the flow of ions. In the applicator of the present invention, current flow in the electrodes is electronic and current flow in the reservoir and through the skin is electrolytic, but it is possible to have some electronic flow along the chain of a polypeptide in an electric field in water or aqueous media.

The values of the electrical variables in the practice of the current invention in vivo are those pertaining to electroosmosis not ionophoresis. The current density may range from about 0.5 ua/cm$^2$ to about 1 ma/cm$^2$, preferably about 0.5 microampere/cm$^2$ to about 10 microampere/cm$^2$ rather than 1 milliampere/cm$^2$ to 5 milliamperes/cm$^2$ values associated with ionophoresis. The voltage impressed for operating the applicator of the present invention ranges from about 1 to about 40 volts rather than the 50 to 100 or more volts advisable for ionophoresis. Likewise the migratory flow of water in an electrolytic field are the much higher values of about 0.001 ml/cm$^2$/hr to about 0.005 ml/cm$^2$/constant of electroosmosis not the typical adventitious values for ionophoresis, following Faraday's law which impels only ions.

It is highly preferred that the current density employed in the present invention be low enough to prevent any irritation, reddening, inflammation, or erythema in the skin of the patient. In addition to the polypeptide drug, there may be salts for physiological balance, buffering agents, biocides, preservatives, disinfectants, antibiotics, or other additives in the composition of the drug reservoir of the electrolytic transdermal device.

It is sometimes useful to add chelating agents to the drug. Some of the metal ions which may be associated with the polypeptide are magnesium, zinc, copper, chromium, cobalt, nickel, iron, and manganese. Many conventional chelating agents may be employed such as the salts of ethylenediaminetetraacetic acid (EDTA). Other conventional chelating agents may also be used.

FIG. 1 shows generally drug applicator 10 comprising outer cover 12 having a raised portion 14 and an outer-edge lip 16 in contact with the skin 18 of the patient. The layered structure of the drug applicator 10 can be any convenient and effective size or shape such as rectangle, oval, circle, or splayed shape to fit crevices at interfaces of body parts. The size of the applicator may range from about 10 cm$^2$ to about 200 cm$^2$ depending on its use and the species, age, and size of the patient.

Applicator 10 often has generally a structure of horizontal layers. The layer shown in FIG. 1 as that closest to the skin 18 is an optional semipermeable membrane 22 through which the drug diffuses for deposition on skin 18. Optional membrane 22 may be constructed of semipermeable cellulose acetate, poly(vinyl chloride), or regenerated cellulose.

Above optional semipermeable membrane 22 is a reservoir, region, or pouch 24 for holding the supply of the drug to be electrolytically delivered. Preferably reservoir 24 defines a closed space and is flexible. Typical materials used in forming pouch 24 are rayon floc, polyurethane sponge, and hydrophilic adhesives. This reservoir may also consist of a hydrophilic gel. For containing the polypeptide solution or suspension of the present invention, reservoir 24 may range from about 0.01 ml to about 15 ml in volume, preferably about 0.15 ml to about 0.9 ml for about a week's continual administration of a polypeptide drug in amounts ranging from about 500 nanograms to 1 mg per day, depending on the size, species, and age of the patient. The gel, pouch, or walls of the reservoir 24 must be microporous enough to transfer of the solvent, solution, or suspension of the polypeptide by the electric field, but not so porous to allow leakage of the suspension or solution of the polypeptide drug. The choice of whether or not to employ optional semipermeable membrane 22 is interrelated with the choice of design and material of reservoir 24, because their functions may overlap.

The next higher layer above reservoir 24 as shown in FIG. 1 comprises extended contact 26 which is preferably the lower face of battery 28. Contact 26 preferably is flexible enough to conform to the surface of the skin and also is electronically conductive. Preferred materials for contact 26 are electric-conducting polymers, carbonized plastic films, or plastic surfaces loaded with highly conductive powdered or solid carbon or graphite.

Battery 28 comprising the next layer may be made up of a group of cells internally connected in series to obtain the desired voltage necessary to obtain the electrophoretic action with the particular polypeptide. Orientation of battery 28 depends on the direction of endosmotic flow which is usually from the anode. With regard to battery 28, it should be noted that any conventional miniaturized battery cells now generally available can be employed, arranged and connected in series to obtain the desired operating voltage. In addition, the technology now exists for batteries made of thin, flexible sheets of an electrically conductive polymer with high surface area relative to its thickness to provide adequate current densities. One such so-called plastic battery is described in "Batteries Today", Autumn 1981, pages 10, 11, and 24. When such a battery is employed, sheets may be layered to place the cells in series, and an effective compromise between number of sheets and surface areas of sheets is achieved by layering them diagonally, as shown somewhat schematically in FIG. 1. Of course, battery selection also depends on such factors as the degree of conformability desired, voltage and current densities required for a specific application, and time of discharge.

In FIG. 1, above battery 28 is electrical contact 32, which preferably is similar in design and material to electrical contact 26 and forms the opposite side of the battery.

Cover 12 encloses all the previously listed layers of drug applicator 10 and is made of flexible, conductive material such as a plastic polymer impregnated with carbon, electrically conductive itself, or metallized on its surface. Insulating material 34 fills the space between the side walls of raised portion 14 and the various aqueous layers containing electrolyte. Suitable insulating materials are polyester, silicones, and any other drug-compatable plastics. Alternatively, a totally insulating cover may envelope all of the working components previously named.

In order for drug applicator 10 to make good contact with and stick to the patient's skin 18 electrically-conductive adhesive 36 is applied under the edge of lip 16. Suitable conducting adhesive materials are those filled with powdered conductors such as carbon or graphite.

It will be seen that the arrangement described above forms a complete electric circuit from one side of battery 28, cover 12, adhesive material 36, skin 18, microporous membrane 22, liquid reservoir 24, and back to battery 28. Also, the reservoir may be divided into separate anode and cathode compartments with an insulator between and the battery in a separate compartment.

The electrical operation of the drug applicator may be carried out in many modes, including that of uniform direct current. The impressed voltage from the power source may be pulsed with a wide variety of pulse width and frequency. A sawtooth voltage or other types of reversing, sinusoidal, or alternating voltage sources are also within the disclosure of this invention.

The types of batteries and their orientation are disclosed inter alia in U.S. Pat. Nos. 4,557,723 and 4,640,689. The types of circuits which may be employed are also disclosed in various of the above-cited related applications.

Table I shows some of the therapeutic polypeptides with commercial or experimental status. The evolutionary relationships, aminoacid sequences, intra- and interrelationships, structures, and activity of polypeptide hormones and drugs are generally known and published. The seventh edition of Goodman and Gilman's "The Pharmacological Basis of Therapeutics", Macmillan, N.Y., 1985 has relevant material. Also see 40th edition of "Physicians' Desk Reference", Medical Economics Co., Oradell, N.J., 1986.

The present invention encompasses the electrolytic transdermal delivery of solutions and suspensions of the numerous polypeptide drugs, hormones, agonists, secretion inhibitors, and regulators of glucose metabolism, water regulation, CNS activity, growth, pain alleviation, blood pressure regulation, cancer alleviation, and other functions for molecules having from about three (cf. thyrotropin releasing hormone) to about 20 (cf. atriopeptin, said to be 21) peptide units. Without being limited by theory, it is believed that the primary mechanism for this electrolytic delivery is by electroosmosis, not ionophoresis, as erroneously subscribed to by the scientific workers in the prior art.

In many cases it is preferred to add cosolvent/cosolute molecules with negative Setschenow constants to the polypeptide drugs of the present invention to facilitate their transdermal delivery, as shown in Table II.

Having described the inventive composition of polypeptide, water structure-breaking solute, and aqueous electrolyte and having described the preferred embodiment of the electrolytic drug applicator for transdermal delivery of polypeptides, we now illustrate the invention in the following Examples. These Examples, however, are intended only to illustrate not limit the scope of the instant invention, which may be carried out by other means and still be covered by the teachings of this disclosure.

EXAMPLE 1

This Example illustrates the preparation of small electrolytic transdermal devices with side-by-side reservoirs and electrodes. Another possible design is that of a "matted-photograph" with the drug reservoir anode surrounded by an insulated frame-shaped cathode, as shown in FIG. 1.

The side-by-side reservoirs and electrodes have a rayon gauze next to the skin (Johnson & Johnson Co., New Brunswich, N.J.). Two matted rayon pads 5 cm $\times$ 8 cm $\times$ 0.5 cm are topped by U-shaped polyester film 0.1 mm thick coated with 0.02 mm layer of conducting graphite paint (Bertek Corp., St. Albans, Vt.) surrounding a central insulator of 0.2 mm Mylar polyester film (duPont Co., Wilmington, Del.). The top surface of the U-shaped graphitized polyester film is connected to a 9 V battery (El Power Corp., Santa Anna, Calif.). The periphery of the felted reservoir pads and electrodes plus an insulating band in the gauze base between them is RTV silicone resin (Dow Corning Co., Midland, Mich.). Surrounding the top and side of the device is surgical adhesive tape (Hy-Tape Surgical Hosiery Corp., New York, N.Y.). Each of the reservoirs can hold 6 ml of aqueous fluid.

EXAMPLE 2

This Example illustrates the use of the present invention to deliver therapeutic amounts of an experimental linear polypeptide having about ten peptide units, useful in the treatment of prostate cancer, compound DUA, a variant of leuprolide acetate.

Four male subjects were fitted: two with large drug applicators (9 cm by 13 cm) active area 37 cm$^2$ on the chest, subjects A and B, and two with small drug applicators (5 cm by 13 cm) active area 11 cm$^2$ on the volar area of the arm, subjects C and D. The large applicators had reservoirs of 0.6 ml; the small 0.15 ml. The solution in the reservoir consisted of 10 percent polypeptide and 1 percent urea.

The battery had a voltage of 9 volts; the current density was 3.5 microamperes/cm$^2$ for the application time of eight hours. During that time the polypeptide was transdermally transported to the extent of 200 microgr./hr for the large and 60 microgr./hr for the small applicators. Blood analysis shows the amount and activity of the delivered hormone in the hormonal response to the delivery of the drug to the four subjects, as follows:

A a five-fold increase in 3 hrs.,
B a four-fold increase in 4 hrs.,
C a triple response in 5 hrs.,
D a 12-fold increase within 6 hrs.

This stimulated response of the subjects is typical of a healthy, adult, male receiving therapeutic subcutaneous bolus injection of this hormone.

MODEL EXAMPLE 1

This Model Example illustrates the application of the present invention to the delivery of lypressin (Diapid, Sandoz Co., East Hanover, N.J.) to the bloodstream of the patient.

Eight beagle dogs are employed. All of them are clipped on the back, washed with castille soap, and fitted with the small animal electrolytic patches of Example 1, four of them without batteries.

The drug reservoir of each patch contains 6 ml. Diapid 50 USP, 0.185 mg lypressin/ml. The return reservoir contains 0.9 percent saline. A current regulator is set to deliver 10 ua/cm$^2$.

Over a period of ten days the total urine output of each dog is measured by standard techniques. It is found that the average total urine volume of the four dogs wearing the powered device of the present invention is significantly lower than that of the average of the four control dogs.

MODEL EXAMPLE 2

This Model Example illustrates the use of the present invention to delivery vasopressin for the treatment of diabetes insipidus.

Six adult male volunteers each having been diagnosed as having diabetes insipidus are tested. Three are fitted with the large-size human patch, as in Example 2, and the three controls are fitted with drug-loaded, identical patches without batteries.

The drug reservoirs of the large electrolytic patches contain 15 ml (300 units) of Pitressin (Parke-aDavis Co., Morris Plains, N.J.). The return reservoir contains 0.9 percent saline buffered to pH 7.2 with ammonium dihydrogen phosphate.

Urine samples are taken from each subject three times per day for five days. It is found that the electrical conductivity of the urine of the subjects wearing the powered Pitressin (vasopressin) electrolyte patches averages significantly higher than that of the three control subjects, showing higher electrolyte content.

MODEL EXAMPLE 3

This Model Example illustrates the use of the present invention to deliver atrial natiuretic factor, atriopeptin, directly to the bloodstream of patients.

Ten adult female volunteers, diagnosed as having hypertension, are chosen for this experiment. All are fitted with the large-size electrolytic transdermal patch, as in Example 2.

The subjects are fitted with patches of the present invention having a drug reservoir containing 5 ml of a 0.01M solution of atriopeptin in 0.1M sodium perchlorate, a salt with negative Setschenow constants. Five control patches have no batteries. The regulated power source is set to give a current density of about 10 ua/cm$^2$, delivering about 200 nanograms of drug per hour.

The blood pressure of the ten subjects is measured four times a day. It is found that the average blood pressure of the five subjects having powered patches is significantly lower than the average of the five controls.

Although the specification and Examples above describe aqueous media, the present invention is equally applicable to nonaqueous media such as the injectable oils familiar to those skilled in the art, such as glycerine, propylene glycol, benzyl alcohol, and the like.

Many other embodiments of this invention will be apparent to those skilled in the art, but such will be within the scope of Letters Patent based on the following claims.

We claim:

1. An electrolytic transdermal patch including an electrical circuit with an electrical power source for delivering at least one drug to the bloodstream of the patient comprising in combination:
    (a) at least one polypeptide having from about three to about 20 peptide units, and
    (b) means for transdermal transport of the polypeptide characterized by a current density from about 0.5 microampere/cm$^2$ to about 1 milliampere/cm$^2$ whereby the skin of the patient is neither irritated nor erythematized.

2. A transdermal patch as in claim 1, wherein the means for transport comprises a battery, an anode, a cathode, a drug reservoir, and barrier means between electrodes.

3. A transdermal patch as in claim 2, further comprising a semipermeable membrane on the skin side of the drug reservoir.

4. A transdemal patch as in claim 1, wherein the current density of the patch is from about 0.5 ua/cm$^2$ to about 10 ua/cm$^2$.

5. A transdermal patch as in claim 1, further comprising at least one compound selected from the group consisting of buffering agents, chelating agents, antioxidants, preservatives, and biocides.

6. A transdermal patch as in claim 1, further comprising an aqueous solvent for the polypeptide.

7. A transdermal patch as in claim 6, further comprising a dissociating cosolvent.

8. A transdermal patch as in claim 7, wherein the dissociating cosolvent is selected from the group consisting of urea, guanidine salt, butanol, 2-butanol, water-soluble amides with more than three carbon atoms, sodium and potassium iodide, sodium perchlorate, sodium butyrate, and any other salt with negative Setschenow constants.

9. A transdermal electrolytic patch for delivering at least one drug directly to the bloodstream of the patient as in claim 1, comprising:
    (a) an active ingredient comprising at least one polypeptide having from three to twenty peptide units having pharmacological activity in an application selected from the group consisting of alleviating diabetes insipidus, gastrointestinal hemmorhage, induction of childbearing labor, antidiuretic, alleviating prostate cancer, inhibition of LH-RH FSH, analgesic, hormonal regulation, insulin regulation, growth hormone inhibition, modulation of blood pressure, regulation of body fluids, and combinations thereof; and
    (b) electrolytic means for transdermal transport of the polypeptide characterized by a current density from about 0.5 microamp/cm$^2$ to about 1 milliamp/cm$^2$, whereby the skin of the patient is neither irritated nor erythematized.

10. A transdermal patch as in claim 9, wherein the polypeptide is selected from the group consisting of vasopressin, desmopression, oxytocin, bypressin, leuprolide acetate, dynorphin A. dynorphin B, met-enkaphalin, leuenkephalin, thyrotropin, releasing hormone, alphal-melancyte stimulating hormone, beta-melancyte stimulating hormone, neurotensin, substance P, somatostatin, angioxensin I, angiotensin II, angiotensin III, atriopeptin, and combinations thereof.

11. A transdermal patch as in claim 9, wherein the electrolytic means comprises a battery, an anode, a cathode, a drug reservoir, and a barrier means between the electrodes.

12. A transdermal patch as in claim 9 further comprising an aqueous solvent for the polypeptide.

13. A transdermal patch as in claim 9, further comprising at least one compound from the group consisting of buffering agents, chelating agents, antioxidants, preservatives, biocides, and dissociating cosolvents with a negative Setschenow constant.

14. A transdermal patch as in claim 9, further comprising current controlling means whereby the current density of the patch is from about 0.5 to about 10 microamps./cm$^2$.

15. A transdermal patch as in claim 13, wherein the dissociating cosolvent is selected from the group consisting of urea, alkylderivatives of urea, guanidine salt, butanol, 2-butanol, water-soluble amides with more than three carnon atoms, sodium iodide, potassium iodide, sodium perchlorate, sodium butyrate, and any other salt with negative Setschenow constants.

16. A transdermal patch as in claim 11, further comprising a semipermeable membrane on the skin side of the drug reservoir.

17. A transdermal patch for delivering at least one drug directly to the bloodstream of the patient comprising in combination:
(a) a circuit including an electrical power source for supplying power to and electrically connected to at least one electrical contact at a drug reservoir and means for controlling the current density of the patch from about 0.5 microampere/cm$^2$ to about 10 microampere/cm$^2$; and
(b) an active ingredient comprising at least one polypeptide having from about three to about 20 peptide units in an aqueous drug reservoir;

whereby the skin of the patient is neither irritated nor erythematized.

18. A transdermal drug patch as in claim 17, further comprising a semipermeable membrane on the patient side of the drug reservoir.

19. A transdermal drug patch as in claim 17, further comprising at least one compound selected from the group consisting of buffering agents, chelating agents, antioxidants, preservatives, and biocides.

20. A transdermal drug patch as in claim 17, wherein at least one polypeptide is LH-RH analog further comprising testosterone.

21. A transdermal drug patch as in claim 17, wherein at least one polypeptide is LH-RH analog further comprising Flutamide.

22. A transdermal drug patch as in claim 17, further comprising covering means over at least part of the drug reservoir.

23. A transdermal patch as in claim 17, further comprising a water-destructuring agent in the active ingredient in the aqueous drug reservoir.

24. A transdermal patch as in claim 23, wherein the water-destructuring agent is selected from the group consisting of urea, alkylderivatives of urea, guanidine salt, butanol, 2-butanol, water-soluble amides with more than three carbon atoms, sodium iodide, potassium iodide, sodium perchlorate, sodium butyrate, any other compound with negative Setschenow constants, and mixtures thereof.

25. A transdermal drug patch as in claim 24, wherein the water-destructuring agent is urea.

26. A transdermal drug patch as in claim 24, wherein the water-destructuring agent is potassium iodide.

* * * * *